United States Patent
Brendel et al.

(10) Patent No.: US 6,874,934 B2
(45) Date of Patent: Apr. 5, 2005

(54) MODULAR X-RAY DIAGNOSTIC APPLIANCE

(75) Inventors: Frank Brendel, Coswig (DE); Franz Fadler, Hetzles (DE); Karlheinz Kaul, Neunkirchen (DE); Stefan Leidenberger, Effeltrich (DE); Hans Liegl, Erlangen (DE); Heinz-Joachim Link, Erlangen (DE); Konrad Pieger, Kirchehrenbach (DE)

(73) Assignee: Siemens Aktiengesellschaft, Münich (DE)

( * ) Notice: Subject to any disclaimer, the term of this patent is extended or adjusted under 35 U.S.C. 154(b) by 102 days.

(21) Appl. No.: 10/312,784

(22) PCT Filed: Jun. 26, 2001

(86) PCT No.: PCT/DE01/02338

§ 371 (c)(1),
(2), (4) Date: Dec. 27, 2002

(87) PCT Pub. No.: WO02/00116

PCT Pub. Date: Jan. 3, 2002

(65) Prior Publication Data

US 2004/0091082 A1 May 13, 2004

(51) Int. Cl.$^7$ ................................................. H05G 1/02
(52) U.S. Cl. ....................................... 378/197; 378/193
(58) Field of Search .............................. 378/193, 195, 378/196, 197, 205, 208, 209, 210

(56) References Cited

U.S. PATENT DOCUMENTS 3,971,949 A * 7/1976 Brather et al. ............... 378/173
4,887,287 A * 12/1989 Cobben ........................ 378/198
5,386,453 A    1/1995 Harrawood et al.
5,410,584 A * 4/1995 Schaefer et al. ............. 378/196
5,822,814 A   10/1998 Van der Ende
5,838,765 A * 11/1998 Gershman et al. .......... 378/196

FOREIGN PATENT DOCUMENTS

| DE | OS 199 33 229 | 3/2000 |
| DE | OS 199 27 480 | 1/2001 |
| EP | 0 251 487 | 1/1988 |
| EP | 0 877 538 | 11/1998 |
| FR | 2 616 650 | 12/1988 |

* cited by examiner

Primary Examiner—David V. Bruce
Assistant Examiner—Chin-Cheng Glen Kao
(74) Attorney, Agent, or Firm—Schiff Hardin LLP

(57) ABSTRACT

A modular X-ray diagnostic appliance has as a first module, a base support, as second module, at least one support for the base support, as a third module, at least one component of an X-ray imaging device, as a fourth module, a support device for an object to be examined, and, as a fifth module, a longitudinal carriage which is arranged above the base support and on which the component is mounted. The base support has support-device coupling elements for coupling the support device thereto, support-coupling elements for coupling the support thereto and component-coupling elements for coupling the component thereto. The component-coupling elements have a fixed and/or floating bearing arranged on the base support and connected to the longitudinal carriage. In a method for producing different series of X-ray diagnostic appliances, in which a structurally identical modular base support and a structurally identical modular support device are used for all series.

3 Claims, 3 Drawing Sheets

MODULAR X-RAY DIAGNOSTIC APPLIANCE

BACKGROUND OF THE INVENTION

1. Field of the Invention

The present invention is directed to a modular X-ray diagnostic appliance and a method for producing different series of X-ray diagnostic appliances.

2. Description of the Prior Art

Various X-ray diagnostic appliances are known which, depending on whether the X-ray emitter is located above or below a support table for an object to be examined, are designated as over-table or under-table X-ray diagnostic appliances. The X-ray emitter can be assigned a radiation receiver which is designed as an X-ray film, as an image amplifier or as a solid-state detector. It is known to arrange the X-ray emitter so that it can be adjusted in relation to the radiation receiver, or to arrange the radiation receiver so that it can be adjusted in relation to the X-ray emitter, or for both the X-ray emitter and the radiation receiver to be arranged so as to be adjustable, so that an object to be examined can, for example, be exposed to radiation from different directions. For this purpose, it is known, for example, to mount the X-ray emitter and the radiation receiver lying opposite one another at the ends of a C-arm. In these X-ray diagnostic appliances, the support table can be mounted in a fixed position or can be adjustable, for example on a pedestal, so that it can be adjusted in height and/or around a swivel axis and/or along its longitudinal axis and/or transverse axis. It is further known to mount an X-ray emitter, the radiation receiver and the support table on a floor column or ceiling column, in each case constituting a separate part. The under-table or over-table X-ray diagnostic appliances in each case form one unit and are each made up of individual parts.

SUMMARY OF THE INVENTION

It is an object of the invention to be able to produce different X-ray diagnostic appliances using uniform or common parts, in order to reduce costs as well as to provide a method for achieving this result.

The above object is achieved in an X-ray appliance in accordance with the invention wherein the X-ray diagnostic appliance is designed as a modular system which has, as a first module, a base support as a second module, at least one support for the base support and, as a third module, at least one component of an imaging device, and wherein system support-coupling elements are formed on the base support for coupling the support thereto, and component-coupling elements are formed on the base support for coupling the component thereto. The modular X-ray diagnostic appliance additionally has, as a fourth module, a support device for an object to be examined. Support-device coupling elements are formed on the base support for coupling the support device thereto. The modular X-ray diagnostic appliance according to the invention also has, as a fifth module, a longitudinal carriage which is arranged above the base support and is connected to a fixed and/or floating bearing.

This modular construction makes it possible to arrange different supports or components on the same base support, so that it is possible to configure different X-ray diagnostic appliances.

The component-coupling elements has a fixed and/or floating bearing arranged on the base support, so that the components, for the purpose of their adjustment, are exactly guided by the fixed bearing and are further supported by the floating bearing. Such a design is also inexpensive.

Arranging the longitudinal carriage on the upper face of the base support has the advantage that the side faces of the base support can be used for coupling many different further modules to it. It is advantageous if the guide rail of the floating bearing is arranged geodetically next to that of the fixed bearing.

It is advantageous for the bearing-device support-device coupling elements to be formed on at least one end face of the base support. In connection with the same base support, it is possible to form an X-ray diagnostic appliance which also has a support device for an object to be examined.

The base support is designed for example as a bar. In cross section, it has in particular the shape of a rectangle, preferably flat and/or horizontal.

If the component is to be adjustable, then it is advantageous to provide the base support with a drive device for the component, in particular a drive device also for different components, which drive device at least assists the personnel when adjusting the component, and the adjustment can preferably be controlled. The drive device can be connected to the longitudinal carriage.

For the modular configuration of the X-ray diagnostic appliance, it is particularly advantageous if a motor of the drive device, and to arrange appropriate a motor of a further drive device, inside the base support. In this way, many free surface areas remain on the outside which can serve as coupling points for potential modules.

A further fixed support, which further modules engage, is preferably arranged on the base support. A radiation receiver is preferably arranged on the further fixed support and/or the support device for the object to be examined is preferably adjustably mounted. For further supporting of the radiation receiver and/or of the bearing device, a further floating bearing is provided which is arranged on a longitudinal bar oriented at least approximately parallel to the longitudinal axis of the base support and spaced apart from the base support. The further support on the floating bearing affords precise guiding. In addition, the fixed bearing is of less complicated construction.

The longitudinal bar is preferably connected to the base support via a transverse bar, in particular via on the support-coupling elements formed on the end face of the base support. A frame for the radiation receiver and/or the support device is thus formed issuing from the base support, and the stability of this frame can be increased by the fact that a further transverse bar engages on the support-coupling elements formed on the other end face of the base support. To ensure that the radiation receiver and/or the support device are at least also assisted in their adjustment, it is advantageous to arrange a further drive device for this purpose on the base support.

A radiation receiver can be arranged above the longitudinal carriage via a telescoping column, and a radiation source can be provided below the longitudinal carriage, spaced from the base support and the longitudinal carriage. An under-table X-ray diagnostic appliance is thus formed from modules.

A radiation source can be arranged above the longitudinal carriage via a cantilevered column arranged on the longitudinal carriage, an over-table X-ray diagnostic appliance is formed in modular fashion.

A C-arm X-ray diagnostic appliance can be formed in modular fashion by means of a holder for a C-arm being mounted on the longitudinal carriage.

A suitable support, in particular for the base support, is a ceiling mounting, or a pedestal which is supported for example on the floor of the examination room.

Via the pedestal, the base support can advantageously be adjusted in height and swiveled around a horizontal axis. Support-coupling elements are advantageously provided on the underside and/or at least one of the sidewalls of the base support, via which elements either the pedestal arranged below the base support or the pedestal arranged laterally next to the base support engages on the support-coupling elements via a connecting element. An X-ray diagnostic appliance can thus be produced in conjunction with different support elements which are also each designed as modules.

The X-ray diagnostic appliance according to the invention is thus characterized in particular by its modular construction, which makes it possible to produce different X-ray diagnostic appliances using the same modules or components. It is thus possible to fall back on basic components, as a result of which the production costs in particular can be reduced.

The above object also is achieved in accordance with the principles of the present invention in a method for producing different series of X-ray diagnostic appliances, wherein a structurally identical modular base support and a structurally identical modular support device are used for all series, and wherein each base support, as a central module, is prepared at different coupling points for coupling all modules thereto that are employed in the series, and wherein the support device and, depending on the particular series, further modules, are arranged on the base support, and wherein the aforementioned further modules include a support for the base support and/or a component of an X-ray imaging device and/or a longitudinal carriage.

DESCRIPTION OF THE PREFERRED EMBODIMENTS

X-ray diagnostic appliances are formed by a number of different components which are combined with one another in accordance with the intended purpose of use. The specific design of the appliance is determined by the manufacturer in accordance with the specifications by the recipient and in accordance with the required performance profiler, and the relevant parts are put together. All the components which are absolutely necessary are present in a basic version of the X-ray diagnostic appliance. In higher-grade configurations, further options are additionally built into the basic version. In a "high-end appliance", all options are available.

X-ray diagnostic appliances also differ in terms of their design in that, in principle, a distinction is made between over-table designs and under-table designs, depending on where the radiation emitter is arranged. In order to make it feasible to assemble all possible combinations and structures, the X-ray diagnostic appliance according to the invention is based on a platform concept which can be used both for under-table appliances and for over-table appliances. The central component of each system is a substantially standardized base support with a number of interfaces for the attachment of further components. The base support generally forms the basis of all the X-ray diagnostic appliances that can be put together, and further components are added depending on the desired configuration. The entire modular system is therefore based on a standardized support. The interfaces, in their simplest form, can be designed as threaded bores onto which further coupling elements can be screwed. In a basic design, the X-ray diagnostic appliance has, apart from the base support, a tiltable table with a motor-driven table panel and a targeting device. By means of the platform concept, the number of parts can be reduced by as much as 70%, and yet all variants can be assembled in a modular fashion.

In FIGS. 1 to 8, the interfaces between the base support and add-on components are described.

Figure 1:
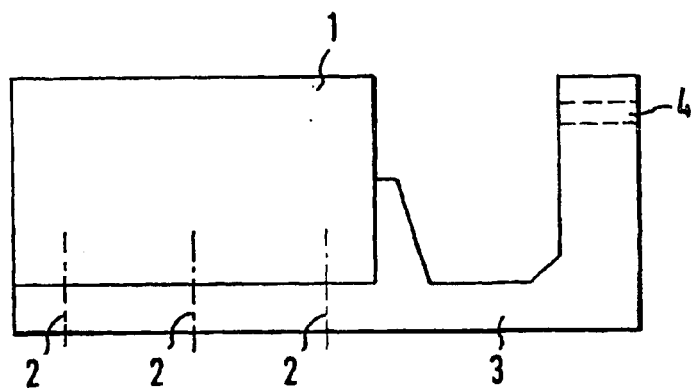
FIG. 1 illustrates the interface between the base support and a bracket in accordance with the invention.

FIG. 1 shows the base support 1 of the modular X-ray diagnostic appliance according to the invention, which base support 1 is constructed as a module and represents the central component of the appliance. The presence of the base support 1 is obligatory in each modular X-ray diagnostic appliance, and all other components are arranged directly or indirectly on the base support 1. In the illustrative embodiment shown in FIG. 1, support-coupling elements designed as screw connections 2 are arranged on the underside of the base support 1 and on one side. The base support 1 is screwed to a bracket 3 via these screw connections 2. The bracket 3 is formed essentially by a horizontal portion which is arranged under the base support 1 and protrudes laterally, and a vertical portion which in its upper area has a supporting seat 4. The bracket 3 can be mounted pivotably on a pedestal via the supporting seat 4. Provision can also be made for the bracket 3 to be adjustable in height, so that a lifting/tilting foot arrangement is obtained. Three different foot variants are used which permit a range of swiveling of −20° to +90°, −45° to 90° and ±90°. The base support 1 is in this case swiveled together with the bracket 3 about a horizontal axis extending through the supporting seat 4. The fact that the supporting seat 4 of the bracket 3 is arranged alongside the base support 1 means that the base support 1 is readily accessible from all sides.

Figure 2:
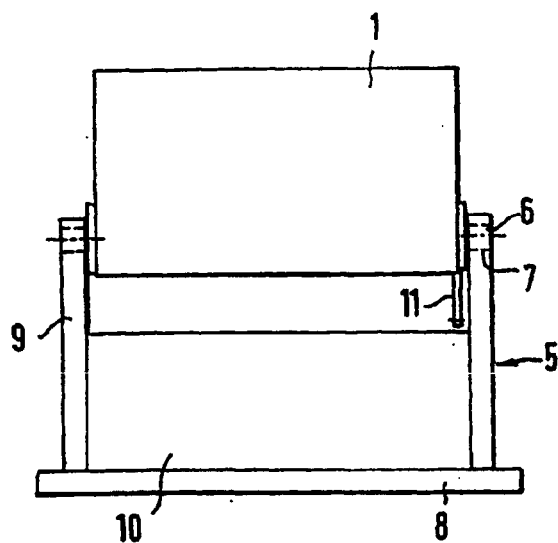
FIG. 2 illustrates the interface between the base support and a tilting foot arrangement in accordance with the invention.

The interface between the base support 1 and a tilting foot arrangement 5, as shown in FIG. 2, represents an alternative to the interface shown in FIG. 1. The support-coupling elements formed on the base support 1 are bearing pins 6 which are arranged opposite one another on the long sides of the base support 1. The bearing pins 6 are screwed or welded onto the base support 1. They serve to mount the base support 1 in supporting seats 7 of a tilting foot arrangement 5. The tilting foot arrangement 5 has a bottom plate 8 and two parallel, spaced-apart sidewalls 9, as well as the supporting seats 7 in the upper area of the sidewall 9. Located between the two sidewalls 9 of the tilting foot arrangement 5, and underneath a covering 10, there is a drive mechanism (not shown) which interacts with a toothed segment 11 arranged on the base support 1 and connected rigidly thereto. Driving the toothed segment 11 results in a pivoting of the base support 1 about the horizontal axis which extends through the supporting seat 7.

Figure 3:
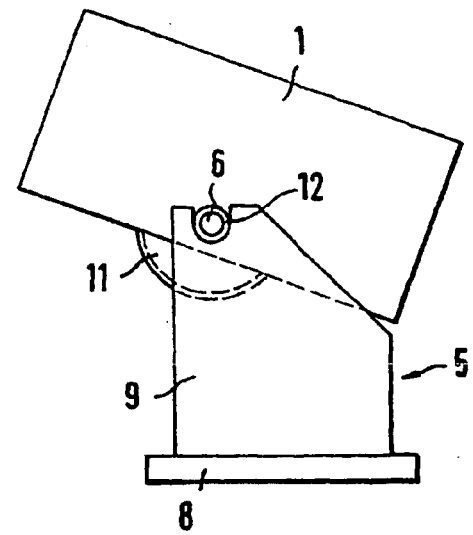
FIG. 3 is a side view of the interface of FIG. 2.

The arrangement from FIG. 2 is shown in a side view in FIG. 3. A ball-bearing 12 is arranged in the bearing seat 7 and serves to receive the bearing pin 6. By means of the tilting foot arrangement 5, the base support 1 and further components arranged thereon can be tilted through a range of swiveling of at least +90° to −20°. Instead of the toothed segment 11 shown here, it is also possible to use a toothed wheel, a toothed belt or a gearing for the adjustment. In a further development of the invention, a lifting unit can also be integrated in the tilting foot arrangement 5 in order to permit adjustment of the height of the base support 1. The interface with the base support is the same, although an additional interface can also be provided. This makes it much easier for the patient to get on and off, and its accessibility is likewise improved. Such a lifting unit includes a gearing unit which is vertically adjustable, for example by means of a chain drive. Other drive mechanisms are also conceivable.

Figure 4:
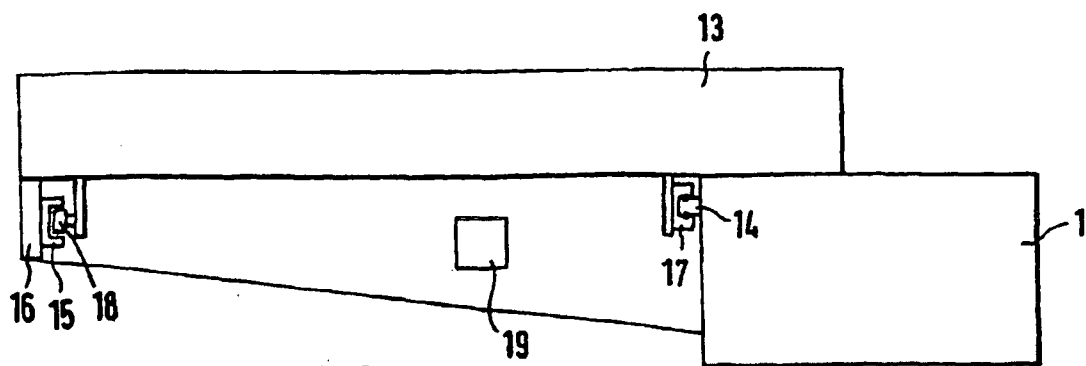
FIG. 4 illustrates the interface between the base support and an over-table targeting device in accordance with the invention.

FIG. 4 shows an interface between the base support 1 and an over-table targeting device 13. For this purpose, component-coupling elements are formed on the side of the base support 1 for the purpose of coupling the component thereto, which coupling elements, in the illustrative embodiment shown, are designed as a combination of a fixed-support guide 14 and a floating-support guide 15. The fixed-support guide 14 is screwed onto the side of the base support 1. The floating-support guide 15 is secured on a bar 16. The arrangement of the fixed support and the floating support can also be chosen vice-versa. The bar 16 is designed as a longitudinal bar and extends parallel to the longitudinal axis of the base support 1. The connection between the bar 16 and the base support 1 is effected via transverse bars (not shown in FIG. 4) which are arranged on both sides at the ends of the bar 16 and, together with the bar 16, form a support. The fixed support guide 14 interacts with corresponding bearing components 17 which are arranged on the underside of the over-table targeting device 13. The fixed bearing can, for example, be a recirculating ball carriage or a slideway carriage. Analogously, the floating-support guide 15 interacts with support components 18 which can, for example, be designed as roller bearings. In this bearing arrangement, an exact guidance is achieved by the fixed support, and further support is achieved by the floating support. Extending between the guides there is a drive train with a drive mechanism 19 which preferably is designed as a chain, but can also be designed as spindle, toothed belt or toothed rod. Via the drive mechanism 19, the longitudinal displacement of the over-table targeting device 13 can be executed by motor. As an alternative to the over-table targeting device 13, an under-table cassette holder can also be provided. The bearing guides 14, 15 permit the securing of different sizes of bars 16 and supports.

Figure 5:
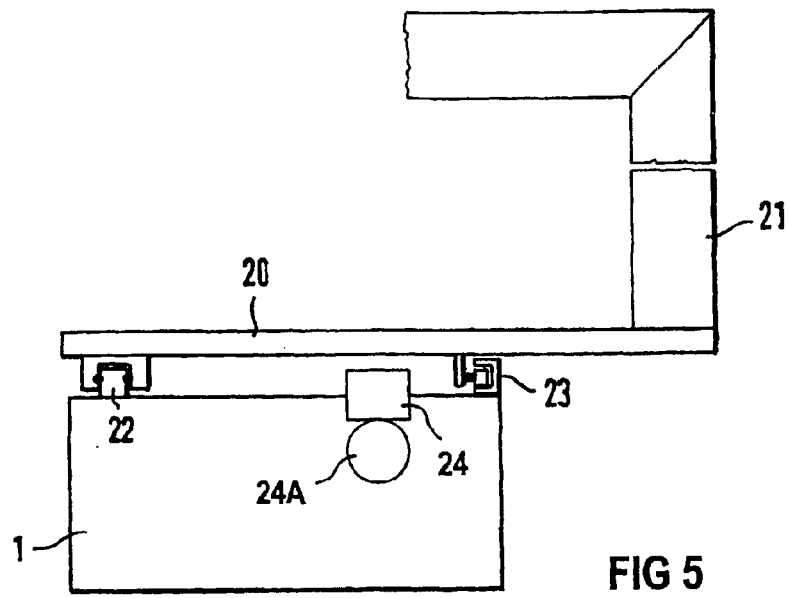
FIG. 5 illustrates the interface between the base support and an over-table radiation column in accordance with the invention.

A further interface arranged on the base support 1 is shown in FIG. 5. This is an interface to a longitudinal carriage 20 with a radiation emitter column 21 arranged thereon. Arranged at the upper end of the radiation emitter column 21 there is a radiation source (not shown in FIG. 5).

For the mounting on the base support 1, the latter has component-coupling elements which are designed as a fixed-support guide 22 and a floating-support guide 23. The support guides correspond to the support guides 14 and 15 shown in FIG. 4. The fixed support guide 22 is formed, for example, by a recirculating ball carriage or a slideway carriage which interacts with a corresponding rail. The floating support guide 23 is a roller bearing which runs, for example, in a C-shape profile matching it. The support guides 22, 23 are arranged on the base support 1 via screw connections so that, if necessary, they can easily be replaced. Located inside the base support 1 there is a motor 24A of a drive mechanism 24 which is indicated only schematically and which displaces the longitudinal carriage 20 and, with it, the radiation emitter column 21 in the longitudinal direction of the base support 1. The support and the longitudinal carriage 20 can be displaced independently of one another.

Figure 6:
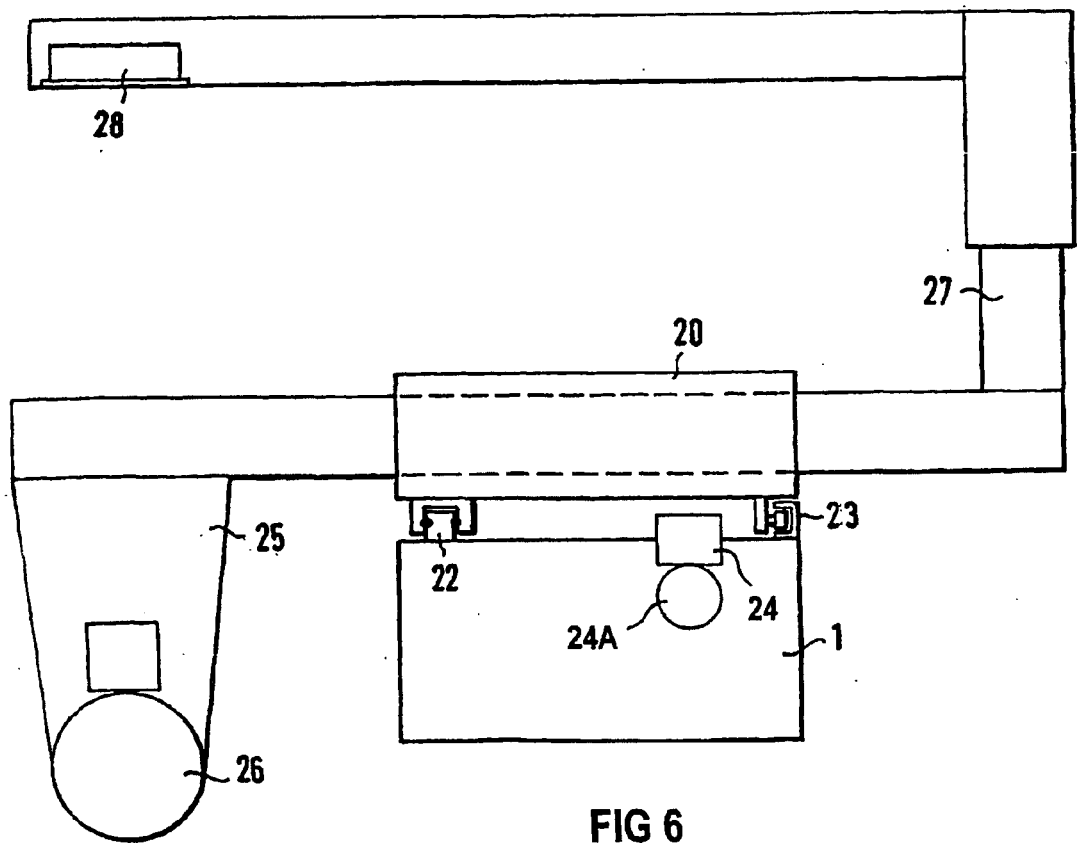
FIG. 6 illustrates the interface between the base support and a longitudinal carriage of an under-table system in accordance with the invention.

FIG. 6 shows a modification of the illustrative embodiment in FIG. 5. The base support 1 with the support guides 22, 23 and with the longitudinal carriage 20 is in this case identical to the previous illustrative embodiment. At one side, the longitudinal carriage 20 has an extension adjoined by a bracket 25 which is arranged below the longitudinal carriage and on which a radiation source 26 is secured. The radiation source 26 is located alongside the base support 1 below the longitudinal carriage 20. Arranged at the opposite side of the longitudinal carriage 20 there is a vertical compression tower 27 which at its upper end carries a targeting device and/or an image receiver 28. The radiation source 26 is oriented to the image receiver 28. The targeting device can also include an X-ray image amplifier or a solid-state detector. Overall, this arrangement represents a modular under-table X-ray diagnostic appliance which can be moved longitudinally relative to the base support 1 via the longitudinal carriage 20.

Figure 7:
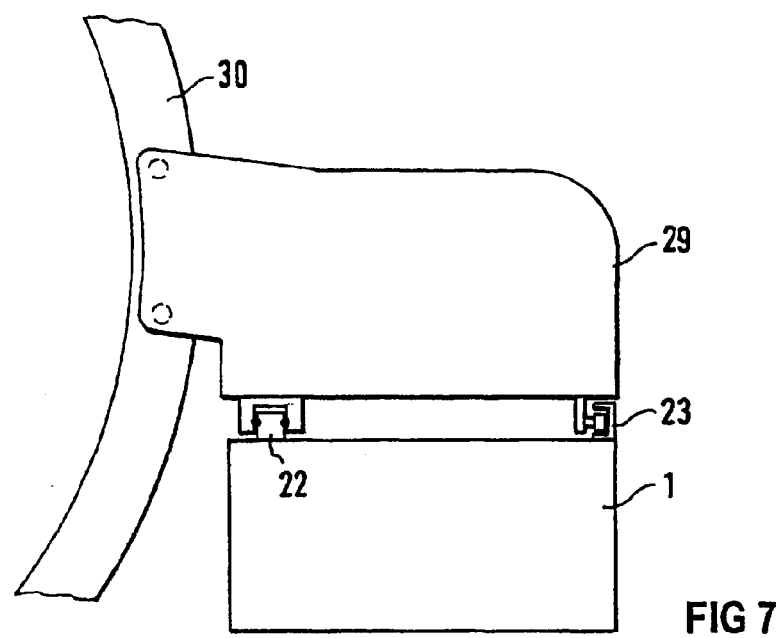
FIG. 7 illustrates the interface between the base support and a C-arm system in accordance with the invention.

A further alternative according to the invention is shown in FIG. 7. As in the illustrative embodiment in FIG. 6, the base support 1 has, on its top face, support guides 22, 23 which are provided for bearing and guiding a C-arm system 30 via a holder 29 representing a longitudinal carriage. The holder 29, which can also permit a transverse displacement and/or rotary movement of the C-arm held on it, is connected rigidly to the C-arm 30, for example screwed onto it, and thereby permits a longitudinal displacement of the C-arm system. The arrangement of the guides and of the drive mechanism corresponds to that of the previous illustrative embodiment.

Alternatively, provision can also be made to secure the holder 29 on a separate longitudinal carriage 20, so that the components of the fixed support guide 22 and of the floating support guide 23 are arranged between the base support 1 and the longitudinal carriage 20.

Figure 8:
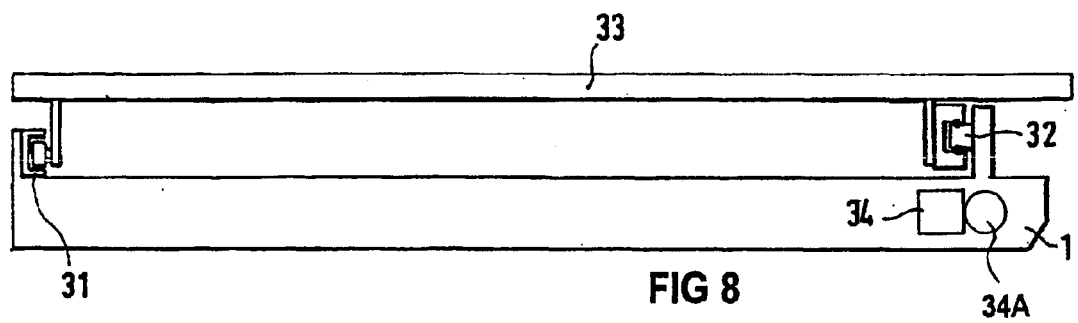
FIG. 8 illustrates the interface between the base support and a support device designed as a table panel in accordance with the invention.

FIG. 8 shows a long side of the base support 1 in a side view. Arranged at both ends of the base support 1 there are supporting-device coupling elements which are designed as floating-support guide 31 and a fixed-support guide 32. The guides 31, 32 serve to guide a support device for an object to be examined, which device is designed as table panel 33. Via a drive mechanism 34 (with motor 34A) arranged in the base support 1, the table panel 33 can be moved by a motor. Together with the support guides 22, 23 and the drive mechanism 24, the table panel 33 can be displaced both in the longitudinal direction and in the transverse direction.

Figure 9:
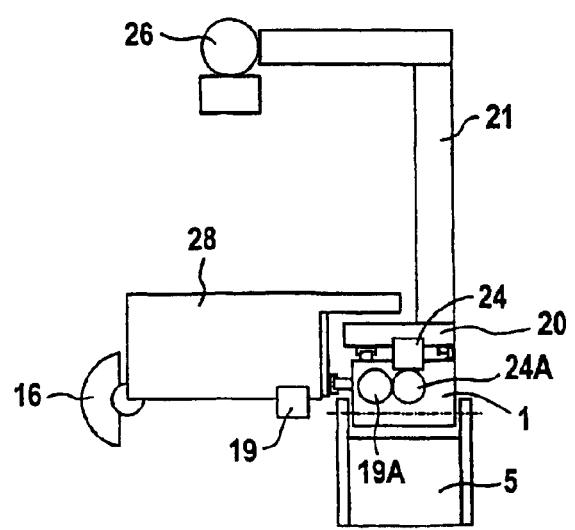
FIG. 9 is an overall view of a modular X-ray diagnostic appliance produced in accordance with the inventive method and having a structure in accordance with the inventive apparatus, with a tilting foot arrangement.

FIG. 9 shows a particularly suitable illustrative embodiment of the invention in an overall view, in which the interfaces described in FIGS. 2, 4 and 5, between the base support 1 and further modules, are realized. The tilting foot arrangement 5 which permits a swiveling of the X-ray diagnostic appliance is situated underneath the support 1. The radiation emitter column 21 with the radiation source 26 is arranged above the base support 1. Laterally in relation to the base support 1, the targeting device/image receiver 28 is mounted so as to be displaceable in the longitudinal direction. Additional support is afforded by the bar 16. Both modules can be moved independently of one another by means of the drive mechanism 19 (with motor 19A in the base support 1) which interacts with the image receiver 28, and by means of the drive mechanism 24 (with motor 24A in the base support 1) which interacts with the radiation emitter column 21. Overall, in this way, a modular X-ray diagnostic appliance is obtained which consists of different components put together in the manner of a system of building blocks.

Although modifications and changes may be suggested by those skilled in the art, it is the invention of the inventors to embody within the patent warranted heron all changes and modifications as reasonably and properly come within the scope of their contribution to the art.

We claim:

1. A method for producing multiple, different series of X-ray diagnostic appliances, comprising the steps of:

in each of a plurality of different series of X-ray diagnostic appliances, employing a structurally identical modular base support and a structurally identical modular support device;

in each of said series, preparing said base support at a plurality of different coupling points for respectively coupling a plurality of modules in the series to said base support;

disposing said support device on said base support and, depending on which of said series is being produced, selecting said modules to be coupled to said base support; and selecting said modules from the group consisting of a support for said base support, a component of an X-ray imaging device, and a longitudinal carriage.

2. A method as claimed in claim 1 wherein said series comprise over-table X-ray diagnostic appliances, under-table diagnostic appliances, and C-arm X-ray diagnostic devices.

3. A method as claimed in claim 1 further comprising the additional step of, within each of said series, selectively equipping said base support with a differing number of components.

* * * * *